(12) United States Patent
Rella

(10) Patent No.: US 9,470,517 B1
(45) Date of Patent: Oct. 18, 2016

(54) PLUME ESTIMATION USING CORRELATION MEASUREMENTS AT ISOLATED SPATIAL POINTS

(71) Applicant: Picarro, Inc., Santa Clara, CA (US)

(72) Inventor: Chris W. Rella, Sunnyvale, CA (US)

(73) Assignee: Picarro, Inc., Santa Clara, CA (US)

( * ) Notice: Subject to any disclaimer, the term of this patent is extended or adjusted under 35 U.S.C. 154(b) by 655 days.

(21) Appl. No.: 13/866,660

(22) Filed: Apr. 19, 2013

Related U.S. Application Data

(60) Provisional application No. 61/636,300, filed on Apr. 20, 2012.

(51) Int. Cl.
| | | |
|---|---|---|
| *G01P 15/00* | (2006.01) | |
| *G01N 31/00* | (2006.01) | |
| *G06K 9/00* | (2006.01) | |
| *G01B 21/02* | (2006.01) | |
| *G01N 1/26* | (2006.01) | |
| *G01N 33/00* | (2006.01) | |

(52) U.S. Cl.
CPC ............... *G01B 21/02* (2013.01); *G01N 1/26* (2013.01); *G01N 33/0062* (2013.01)

(58) Field of Classification Search
CPC .. G01N 33/0062; G01N 1/26; G01N 1/2273; G01N 21/3504; G01N 33/0004; G01N 2201/025; G08B 21/12
USPC ...... 702/3, 24, 127, 142; 382/100, 154, 191, 382/207, 294; 73/23.2, 23.28
See application file for complete search history.

(56) References Cited

U.S. PATENT DOCUMENTS

| | | | |
|---|---|---|---|
| 8,284,986 B2 | 10/2012 | Wolowelsky et al. | |
| 8,510,059 B2 * | 8/2013 | Prince ................ | G01N 33/0062 702/142 |
| 2010/0094565 A1 | 4/2010 | Prince et al. | |

* cited by examiner

*Primary Examiner* — An Do
(74) *Attorney, Agent, or Firm* — Lumen Patent Firm

(57) ABSTRACT

Repeated simultaneous concentration measurements at spatially separated points are used to provide information on the lateral spatial extent of a gas plume. More specifically the spatial correlations in this data provide this information. Fitting a gas plume model directly to this multi-point data can provide good estimates of total plume emission. The distance between the plume source and the measurement points does not need to be known to provide these estimates. It is also not necessary to perform any detailed atmospheric modeling.

7 Claims, 3 Drawing Sheets

PLUME ESTIMATION USING CORRELATION MEASUREMENTS AT ISOLATED SPATIAL POINTS

CROSS REFERENCE TO RELATED APPLICATIONS

This application claims the benefit of U.S. provisional patent application 61/636,300, filed on Apr. 20, 2012, and hereby incorporated by reference in its entirety.

FIELD OF THE INVENTION

This invention relates to gas plume estimation.

BACKGROUND

Gas concentration measurements are often employed to measure and/or monitor emissions into the atmosphere. Typically, a source of emissions will result in an emission plume in the atmosphere, and the main quantity of interest is often the total amount of emission in the plume. A concentration measurement at a single point is not sufficient for this task. Attempts have been made to use multi-point measurements, combined with detailed atmospheric modeling (e.g., including a turbulence model for the atmosphere) to provide plume emission estimates. However, these approaches suffer from undesirable model complexity, and the results are often disappointing in practice.

Another known approach is to take measurements over a long period of time (e.g., tens of minutes). Averaging these measurements can reduce the effect of the stochastic variability of the propagating plume sufficiently such that fitting the results of such data averaging to a simple plume model (e.g., a Gaussian plume model) can provide adequate results in some cases. However, formulating the model for the plume requires detailed knowledge of the atmosphere, and understanding of the atmospheric flow over the neighboring terrain, including obstacles. In addition, one must also know the distance to the leak and the height of the leak above ground. Any errors in the formulation of the model can lead to an unwanted bias in the reported emission rate results.

Another approach is to directly measure the emission rate by physically enclosing the leak with an impermeable surface (such as a chamber or bag), and then measuring the rate of increase of concentration in the enclosed volume. In many cases, a known flow of clean gas is injected into the volume, such that the concentration in the enclosed volume will asymptotically approach a value which is related to the emission rate of the gas, given the injection rate of the clean gas. However, this method requires physical access to the leak (or leaks), is labor intensive, and prone to underestimation bias if not all the leaks in a given facility are identified.

Accordingly, it would be an advance in the art to alleviate these limitations of complex modeling or direct access to the leak.

SUMMARY

The present approach is based on the observation that an emission plume tends to maintain its integrity (i.e., its lateral spatial concentration profile) as it varies in time. In other words, the main time dependence of the plume can be regarded as a meandering of the plume in the background atmosphere. As a result, repeated simultaneous concentration measurements at spatially separated points can provide information on the lateral spatial extent of the plume. For example, consider two vertically separated points A and B. Repeated simultaneous concentration measurements at A and B provide concentration data $C_{Aj}$ and $C_{Bj}$, where j is an index. The spatial correlation of these concentrations (as can be visualized using a scatter plot of $C_{Aj}$ vs. $C_{Bj}$) can be used to estimate the vertical extent of the plume. Similarly, if points A and C are horizontally separated, then the spatial correlation of $C_{Aj}$ vs. $C_{Cj}$ can be used to estimate the horizontal extent of the plume. Once the horizontal and vertical extent of the plume have been estimated, the plume emission can be estimated using a simple plume model (i.e., no plume meandering in the model), and the average wind speed perpendicular to the A-B-C plane.

DETAILED DESCRIPTION

Figure 1:
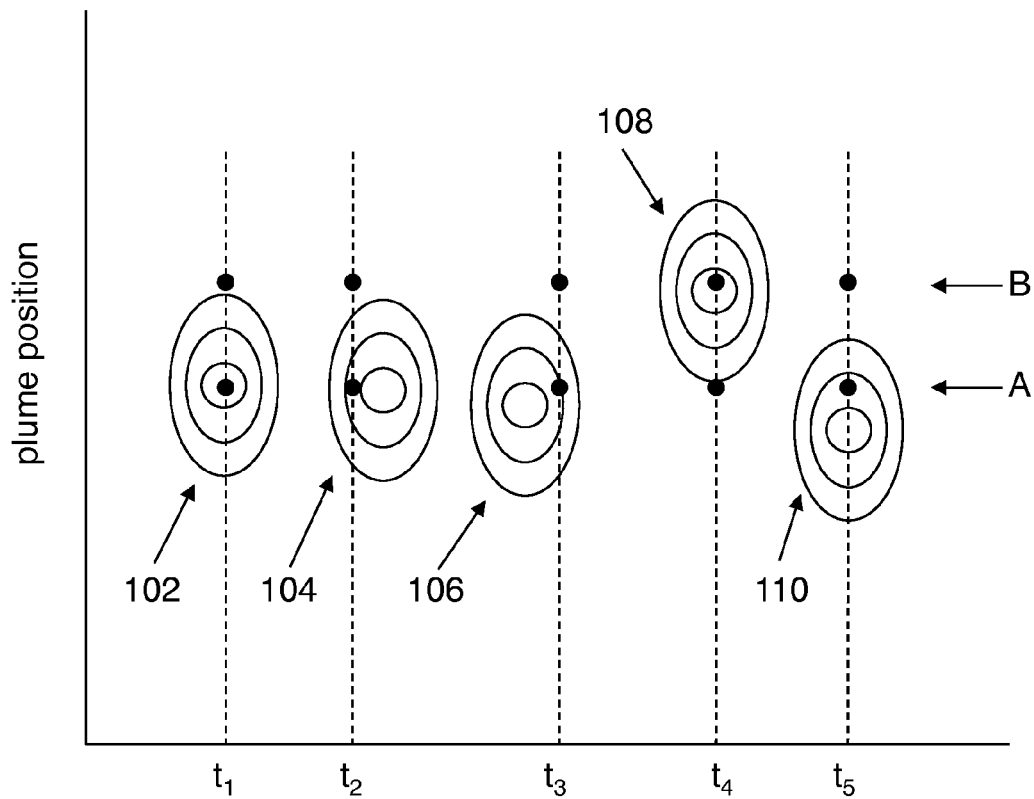
FIG. 1 shows examples of several plume locations relative to two fixed measurement points.

As indicated above, the present approach is based on the assumption that the time dependence of measured concentration from an emission plume is mainly due to meandering of the plume within the atmosphere. FIG. 1 shows examples of several plume locations relative to two fixed measurement points A and B that are vertically separated. At time $t_1$, the plume location is shown by 102. Similarly, at times $t_2$, $t_3$, $t_4$, and $t_5$, the plume locations are shown by 104, 106, 108, and 110 respectively.

Figure 2:
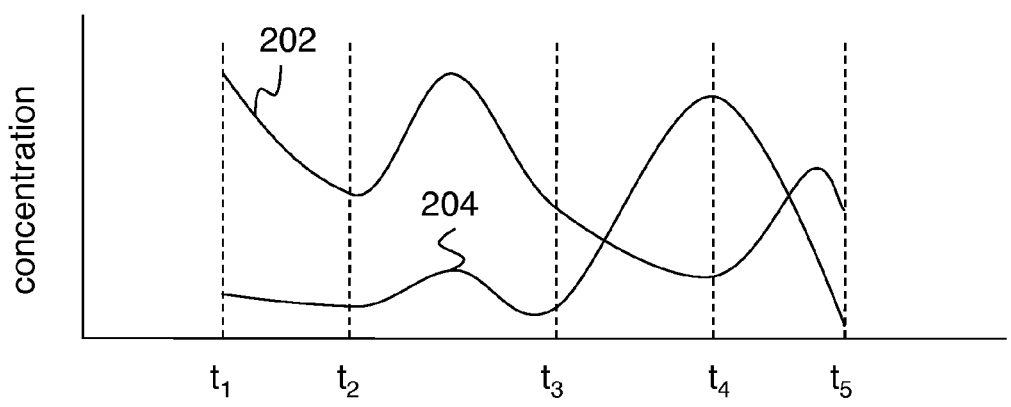
FIG. 2 schematically shows concentration measurements to be expected at the measurement points for the example of FIG. 1.

FIG. 2 schematically shows concentration measurements to be expected at the measurement points for the example of FIG. 1. Here curve 202 is the measured concentration at point A, and curve 204 is the measured concentration at point B. For example, when the plume location is at 102 (i.e., nearly centered on point A), the measured concentration at point A (i.e., curve 202 at time $t_1$) is higher than the measured concentration at point B (i.e., curve 204 at time $t_1$).

From these drawings, it is apparent that as the plume moves relative to measurement points A and B, the measured concentrations will tend to change in related ways. For example, if we assume that the plume moves horizontally from right to left between times $t_2$ and $t_3$, we expect the measured concentrations to move together (i.e., either both increasing or both decreasing), as shown on FIG. 2 between times $t_2$ and $t_3$.

However, the behavior is different if the plume moves vertically with respect to these measurement points. For example, if we assume that the plume moves vertically downward between times $t_4$ and $t_5$, we expect the measured concentrations to move opposite to each other (i.e., one increasing and the other decreasing), as shown on FIG. 2 between times $t_4$ and $t_5$. This example demonstrates that simple averaging of measured results can result in a significant loss of information (e.g., these informative correlations would disappear upon averaging the raw data).

An exemplary method for estimating the width w of a gas plume can include the following steps:

1) performing gas concentration measurements at two or more separated measurement points. Each data point is a simultaneous concentration measurement at the measurement points.

2) providing a time-independent gas plume model having at least w as a fitting parameter. The gas plume model also includes parameters for plume position.

3) fitting the gas plume model to the multi-location data points. The plume position is allowed to be a random variable to enable fitting to observed scatter in the data points. An estimate w* of the plume width is provided as an output.

Several features of this exemplary method are noteworthy. First, it is assumed that the data points are simultaneous multi-point measurements. If the multi-point data is acquired sequentially (as can often be convenient in practice), the raw data can be registered to a common time axis (e.g., by suitable interpolation methods) to provide the simultaneous multi-point measurements.

Second, for our purposes, a model is time-independent if it has no explicit dependence on time. However, time-independent models as defined herein can include time-dependent effects in an implicit manner. For example, the centroid of the plume in the measurement plane can vary in time (e.g., as shown on FIG. 1). The plume model includes the position of the center of the plume (e.g., transverse coordinate $y_0$ and $z_0$) as parameters. In reality, these coordinates are functions of time (i.e., $y_0(t)$ and $z_0(t)$). In the present work, this time dependence is handled by letting $y_0$ and $z_0$ be random variables in the fitting to the multi-point correlation data. This is in sharp contrast to conventional approaches that either 1) try to perform dynamical modeling explicitly relating to the time dependence of $y_0(t)$ and $z_0(t)$, e.g., by using measurements of atmospheric parameters such as stability class to predict the meander of the plume, or 2) try to eliminate this time dependence completely by averaging data prior to fitting the plume model. As another example, the plume width w can be modeled as a random variable. This amounts to implicitly accounting for a possible time dependence of plume width by allowing w to be a random variable in the model fitting. A benefit of this approach is that it naturally provides a variance associated with the reported width estimate w*, from which one can get an idea of how reliable the estimate w* is.

Figure 3:
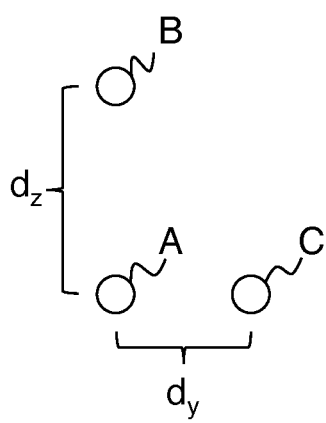
FIG. 3 shows a preferred arrangement of measurement points.

FIG. 3 shows a preferred arrangement of measurement points. Here measurement points A and B are vertically separated by a distance $d_z$ and measurement points A and C are horizontally separated by a distance $d_y$. Such an arrangement is preferred in practice because it can provide estimated widths $w_y$ and $w_z$ for both transverse dimensions of a gas plume. For example, the above-described method can be performed in two orthogonal directions. Here points A, B and C are in the same plane. Measurements relating to the two orthogonal directions can be performed either simultaneously or sequentially. If these measurements are performed sequentially, they can be put on a common time axis (e.g., by suitable interpolation methods) to provide simultaneous multi-points data. In this example, the data points can be triples $(C_A(t_i), C_B(t_i), C_C(t_i))$. Here $C_A$, $C_B$, and $C_C$ are measured concentrations at points A, B and C, and $t_i$ is a time index.

There are many possible analysis techniques for recovering the plume width from the multi-point correlation data. We describe one such method here, which uses a Markov-Chain Monte Carlo technique (in particular, a Metropolis-Hastings algorithm) to find an optimal set of plume characteristics, assuming a single peaked Gaussian distribution of concentration vs. transverse space, with different widths along the transverse horizontal and vertical axes y and z. The density of scatter points in the input 'A' vs. 'B' plane (or the input 'A'-'B'-'C' volume) is used as data to be optimized. Variables included in the Monte Carlo simulation are plume widths, plume centroid, and plume concentration peak height. Although costly in computing time, the advantage of this analysis technique is that it produces not only the nominal plume widths and peak heights that are needed to compute the emission rate, but also produces uncertainties for these quantities to be included in the overall uncertainty of the measurement.

Figure 4:
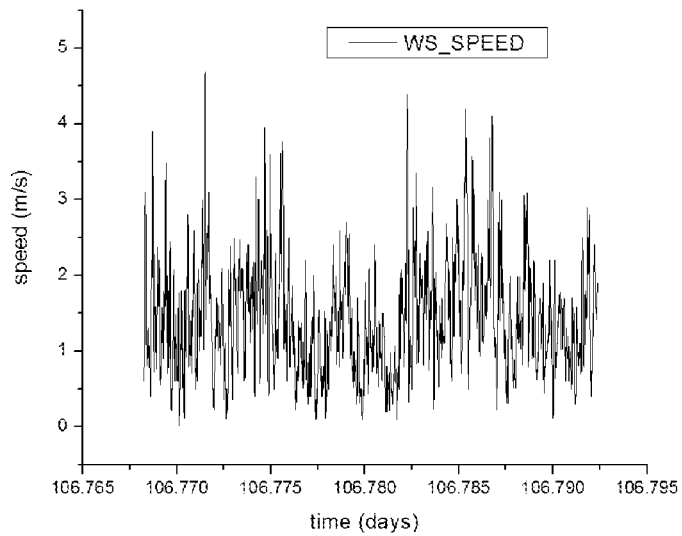
FIG. 4 shows an example of measured wind speed.
Figure 5:
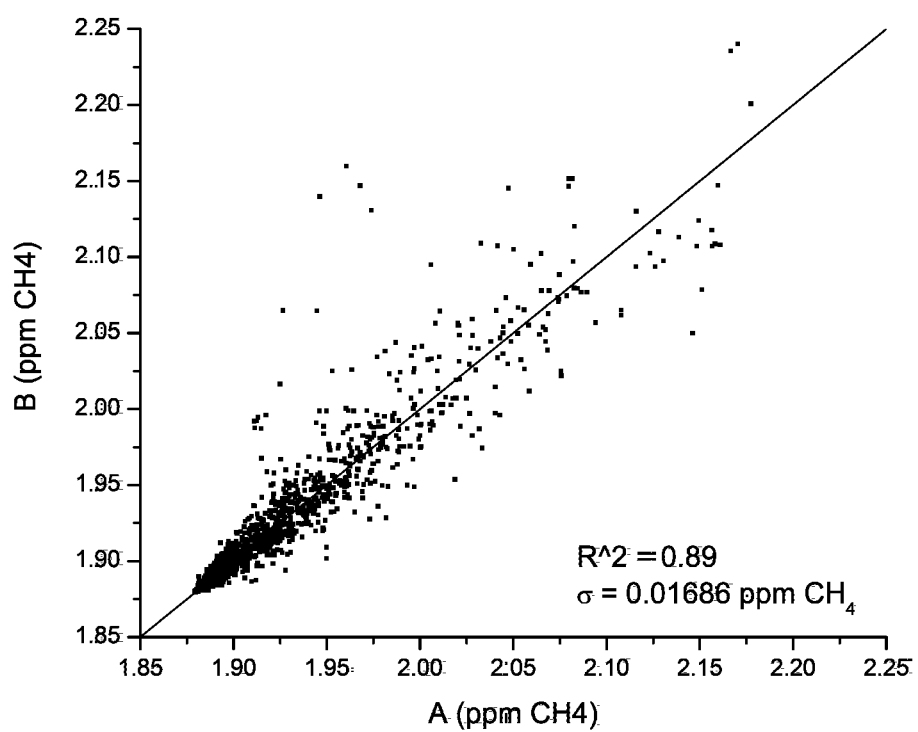
FIG. 5 shows an exemplary correlation plot for two independent measurements at the same point.

Methods according to these principles have been tested in practice, and have performed well. In a first experiment, methane was released at a known rate of 500 sccm (standard cubic centimeters per minute). Three measurement points were located 21 m from the source arranged as in FIG. 3, with a vertical separation of 1.5 m and a horizontal separation of 1.8 m. FIG. 4 shows the measured wind speed for this experiment. FIG. 5 shows an exemplary correlation plot for two independent measurements at the same point 21 m from the source. FIG. 5 is included to show the level of noise in the data that is often encountered in practice. Ideally, the A-B correlation would be perfect because points A and B are co-located, but because of independent errors in the two measurements, a significant level of scatter is observed.

Figure 6A:
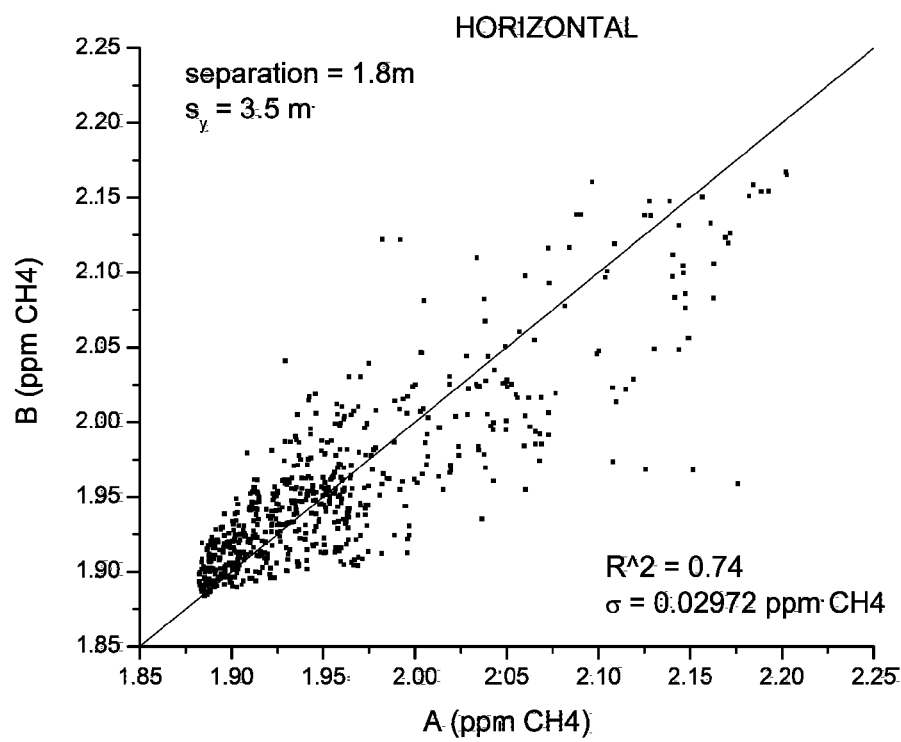
FIG. 6A shows an exemplary correlation plot for two measurement points separated horizontally by 1.8 m.
Figure 6B:
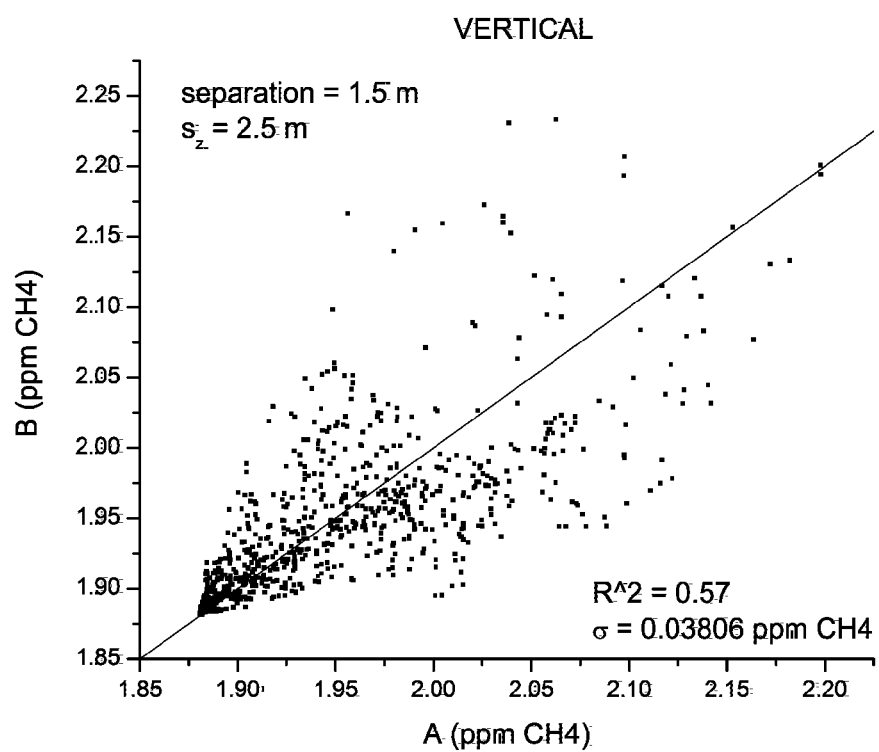
FIG. 6B shows an exemplary correlation plot for two measurement points separated vertically by 1.5 m.

FIG. 6A shows the correlation plot for the two measurement points separated horizontally by 1.8 m. FIG. 6B shows the correlation plot for the two measurement points separated vertically by 1.5 m. For both of these plots, it is apparent that the correlation is significantly less than that seen on FIG. 5, as a result of the separation of the measurement locations in FIGS. 6A-B. However, it is also the case that significant correlations remain, which are exploited in the present approach.

We fit these data to a Gaussian plume model $$C(x, y, z) = C_{peak} \exp\left[-\frac{(y-y_0)^2}{2w_y^2} - \frac{(z-z_0)^2}{2w_z^2}\right]$$

Here $y_0$ and $z_0$ are plume positions (random variables in the fitting). The total emissions Q* in this plume is the y-z surface integral of the product of C(y,z) and the surface normal wind speed V, for all y and positive z, which is approximately given by $$Q^* = \pi w_y w_z V C_{peak}$$

The average wind speed V is a measured value that is provided as an input to the fitting, and Q* is the estimated source emission rate. This fitting process gives widths $w_y=3.5$ m and $w_z=2.5$ m, a peak concentration of 0.22 ppm, and the average wind speed was 1.6 m/s. This gives an estimated plume emission Q* of 527 sccm, which compares well with the actual Q value of 650 sccm. It is noteworthy that the distance between the measurement points and the source does not need to be known (or even estimated) in order to obtain the source emission rate estimate Q*. The only atmospheric parameter used is average wind speed (measured perpendicular to the plane of the measurement points). No absolute wind direction measurements are needed. No estimates of atmospheric stability class or turbulent energy are needed.

Table 1 shows results from a second experiment. Here the first line is from the above described experiment, and the second line relates to a second experiment.

TABLE 1 results for source emission estimates

| $Q_{actual}$ (sccm) | distance (m) | $w^*_y$ (m) | $w^*_z$ (m) | $C_{peak}$ (ppm) | V (m/s) | $Q^*$ (sccm) |
|---|---|---|---|---|---|---|
| 650 | 21 | 3.5 ± 0.4 | 2.5 ± 0.5 | 0.22 | 1.6 | 527 |
| 3,400 | 49 | 4.9 ± 0.5 | 7.4 ± 0.7 | 0.17 | 3.0 | 3490 |

Here we see that good results are obtained, especially given the simplicity of the approach.

The measured correlations between separated measurement points are governed by the spatial extent of the plume along the axis connecting the two points relative to the distance between the two points. When the distance is much greater than the characteristic width of the plume, then the two input points will be completely uncorrelated. When the distance is much smaller than the characteristic width of the plume, then the points are well-correlated. Preferably the user can select the distance between the two points such that the inlet separation is the order of the width of the plume. In practice, unless the width of the plume is known beforehand, the user can select the distance between the two points such that the distribution of measurement points in the 'A'-'B' shows a significant yet not complete degree of correlation. Such a spacing between measurement points is preferred because it produces the most informative correlations for determining plume width parameters.

The invention claimed is:

1. A method for estimating a spatial width w of a gas plume, the method comprising:
    performing multiple gas concentration measurements at two or more separated measurement points, wherein each data point is a simultaneous concentration measurement at the measurement points;
    providing a time-independent gas plume model having at least the spatial width w as a fitting parameter, wherein the gas plume model also includes parameters for plume position; and
    fitting the gas plume model to the data points, wherein the plume position is allowed to be a random variable to enable fitting to observed scatter in the data points, and wherein an estimate w* of the plume spatial width w is provided as an output;
    wherein the method does not depend on a distance between the measurement points and the gas source.

2. A method for estimating widths $w_y$ and $w_z$ of a gas plume, the method comprising:
    performing the method of claim 1 in two orthogonal directions y and z;
    wherein all measurement points are in a common measurement plane.

3. The method of claim 2, wherein the measurement points include three points having y-z coordinates (0,0), ($d_y$,0), (0,$d_z$).

4. A method for estimating total emission from a gas source, the method comprising:
    performing the method of claim 2 to determine widths $w_y$ and $w_z$;
    measuring an average wind speed $v_x$ in a direction perpendicular to the measurement plane; and
    estimating total plume emission using the data points and a plume emission model that includes at least $v_x$, $w_y$ and $w_z$ as parameters.

5. The method of claim 4, wherein the total plume emission estimate is completely determined by fitting parameters of the gas plume model and $v_x$.

6. The method of claim 2, wherein measurements relating to the two orthogonal directions are performed simultaneously.

7. The method of claim 2, wherein measurements relating to the two orthogonal directions are performed sequentially and then registered to a common time axis to provide the simultaneous concentration measurement at the measurement points.

* * * * *